(12) United States Patent
Reunamaki et al.

(10) Patent No.: US 10,864,159 B2
(45) Date of Patent: Dec. 15, 2020

(54) METHOD AND COMPOSITION FOR TREATING OCULAR HYPERTENSION AND GLAUCOMA

(71) Applicants: Santen Pharmaceutical Co., Ltd., Osaka (JP); AGC Inc., Tokyo (JP)

(72) Inventors: Timo Reunamaki, Tampere (FI); Pertti Pellinen, Lempaala (FI); Olli Oksala, Tampere (FI); Kari Lehmussaari, Tampere (FI)

(73) Assignees: SANTEN PHARMACEUTICAL CO., LTD., Osaka (JP); AGC INC., Tokyo (JP)

( * ) Notice: Subject to any disclaimer, the term of this patent is extended or adjusted under 35 U.S.C. 154(b) by 0 days.

(21) Appl. No.: 16/010,739

(22) Filed: Jun. 18, 2018

(65) Prior Publication Data

US 2018/0289618 A1   Oct. 11, 2018

Related U.S. Application Data

(62) Division of application No. 12/995,351, filed as application No. PCT/JP2009/060211 on May 28, 2009, now Pat. No. 9,999,593.

(30) Foreign Application Priority Data

May 30, 2008 (EP) .................................... 08397513

(51) Int. Cl.

| A61K 9/00 | (2006.01) |
| A61K 9/08 | (2006.01) |
| A61K 31/5575 | (2006.01) |
| A61K 47/02 | (2006.01) |
| A61K 47/10 | (2017.01) |
| A61K 47/18 | (2017.01) |
| A61K 47/26 | (2006.01) |
| A61P 27/06 | (2006.01) |

(52) U.S. Cl.
CPC .............. *A61K 9/0048* (2013.01); *A61K 9/08* (2013.01); *A61K 31/5575* (2013.01); *A61K 47/10* (2013.01); *A61K 47/183* (2013.01); *A61K 47/26* (2013.01); *A61P 27/06* (2018.01); *A61K 47/02* (2013.01); *Y02A 50/30* (2018.01); *Y10S 514/913* (2013.01)

(58) Field of Classification Search
None
See application file for complete search history.

(56) References Cited

U.S. PATENT DOCUMENTS

| 4,778,815 | A | 10/1988 | Cash |
| 5,409,125 | A | 4/1995 | Kimber et al. |
| 5,614,172 | A | 3/1997 | Geimer |
| 5,631,287 | A | 5/1997 | Schneider |
| 5,807,892 | A | 9/1998 | Klimko et al. |
| 5,883,108 | A | 3/1999 | DeSantis |
| 5,886,035 | A | 3/1999 | Shirasawa et al. |
| 6,096,783 | A | 8/2000 | Hellbert |
| 6,235,781 | B1 | 5/2001 | Weiner |
| 6,241,124 | B1 | 6/2001 | Hoyt |
| 6,329,426 | B1 | 12/2001 | Ueno |
| 6,342,524 | B1 | 1/2002 | Hellberg et al. |
| 6,344,477 | B1 | 2/2002 | Sharif |
| 6,486,208 | B1 | 11/2002 | Castillo et al. |
| 7,721,901 | B1 | 5/2010 | Von Spreckelsen et al. |
| 8,772,337 | B2 | 7/2014 | Pilotaz et al. |
| 2003/0152631 | A1 | 8/2003 | Morishima et al. |
| 2004/0063607 | A1 | 4/2004 | Fetz et al. |
| 2004/0097592 | A1 | 5/2004 | Morishima et al. |
| 2005/0287325 | A1 | 12/2005 | Baker et al. |
| 2006/0069162 | A1 | 3/2006 | Asada et al. |
| 2006/0100288 | A1 | 5/2006 | Bague et al. |
| 2006/0199863 | A1 | 9/2006 | Kimura et al. |
| 2006/0205725 | A1* | 9/2006 | Ueno ................... A61K 9/0048 514/235.5 |
| 2006/0270735 | A1 | 11/2006 | Deaciuc et al. |
| 2007/0244196 | A1 | 10/2007 | Kimura et al. |
| 2007/0248697 | A1 | 10/2007 | Morishima et al. |
| 2008/0139648 | A1 | 6/2008 | Kado et al. |
| 2008/0269353 | A1 | 10/2008 | Takada et al. |
| 2009/0264523 | A1 | 10/2009 | Asada et al. |

FOREIGN PATENT DOCUMENTS

| CN | 1187486 | 7/1998 |
| CN | 1249687 | 4/2000 |
| CN | 1272063 | 11/2000 |

(Continued)

OTHER PUBLICATIONS

Teaching and Research Group of Pharmaceutics, Nanjing Pharmaceutical College, Pharmaceutics (the Second Edition) (Mar. 1985) with English Translation (cited in CN Patent No. 01815617.7), pp. 90-98.

Nanjing Pharmaceutical College, Pharmaceutics (Mar. 1978) with English Translation (cited in CN Patent No. 01815617.7), pp. 304-314.

Summons to attend oral proceedings pursuant to Rule 115(1) EPC received in EP Application No. 14 001 862.3.

Written Administrative Appeal regarding Chinese Invention Patent No. 200980119724.5 with English Translation dated Feb. 11, 2018.

People's Republic of China Beijing Higher People's Court Administrative regarding Chinese Invention Patent No. 01815617.7 with English Translation dated Sep. 27, 2018.

(Continued)

*Primary Examiner* — Gigi G Huang
(74) *Attorney, Agent, or Firm* — Buchanan Ingersoll & Rooney PC

(57) ABSTRACT

The present invention relates to an ophthalmic aqueous composition containing PGF2α analogues for treating ocular hypertension and glaucoma, to a method for treating ocular hypertension and glaucoma by administering said composition to a subject in need of such treatment, and to a method for increasing aqueous solubility and stability of PGF2α analogues in an aqueous composition.

5 Claims, 2 Drawing Sheets

(56) References Cited

FOREIGN PATENT DOCUMENTS

| | | |
|---|---|---|
| CN | 1438898 | 8/2003 |
| CN | 1457256 | 11/2003 |
| CN | 101072568 | 11/2007 |
| EP | 0 603 800 A1 | 6/1994 |
| EP | 0 850 926 A2 | 7/1998 |
| EP | 0930296 A1 | 7/1999 |
| EP | 1 011 728 A1 | 6/2000 |
| EP | 1 115 406 A2 | 7/2001 |
| EP | 1321144 | 6/2003 |
| EP | 1 349 580 A1 | 10/2003 |
| EP | 1 547 599 A1 | 6/2005 |
| EP | 1 666 043 A1 | 6/2006 |
| EP | 1825855 | 8/2007 |
| EP | 1 829 545 A1 | 9/2007 |
| EP | 1 905 453 A1 | 4/2008 |
| EP | 1 916 002 A1 | 4/2008 |
| JP | 6-107547 | 4/1994 |
| JP | H06-55640 | 7/1994 |
| JP | 63-313728 | 12/1998 |
| JP | T 2002-520368 | 1/2000 |
| JP | A 2002-161037 | 6/2002 |
| JP | 20060503913 | 2/2006 |
| JP | A 2006-187602 | 7/2006 |
| KR | 19980064718 | 10/1998 |
| KR | 10-2003-0029981 | 4/2003 |
| WO | WO 98/41208 A1 | 9/1998 |
| WO | 0 969 846 A1 | 1/2000 |
| WO | WO 0003736 | 1/2000 |
| WO | WO 00/18316 A2 | 4/2000 |
| WO | WO 00/59851 | 10/2000 |
| WO | WO 02/051452 A1 | 7/2002 |
| WO | WO 2004006826 | 1/2004 |
| WO | WO 2004037267 | 5/2004 |
| WO | WO 2007/042262 A2 | 4/2007 |

OTHER PUBLICATIONS

Machine translation of: The authorization to place the product in the market for Taflotan, issued Apr. 30, 2009 (Date of Revision of the Text is Aug. 19, 2009), by the Danish "Laegemiddelstyrelsen"; see especially points 2, 3, 6.1, and 9. (7 pages).
Japanese Office Action dated Sep. 9, 2013, issued in corresponding Japanese Application No. 2011-511256, and English translation.
An English Translation of the Office Action (with Singapore Written Opinion and Singapore Search Report) dated Apr. 13, 2012 issued in corresponding Singaporean Patent Application No. 201008366-5. (20 pages).
Trial Brief filed on Mar. 27, 2015, in Korean Patent No. 854056.
Trial Brief filed on Apr. 10, 2015, in Korean Patent No. 854056.
Pharmacology Textbook (1995), Section 7-2-2, "Use of Additives (Antioxidants and Preservatives)", pp. 178-180 (with English translation) (latest revision 2004).
ChemIDplus—A Toxnet Database, Substance Name Edetate Sodium, U.S. National Library of Medicine, Downloaded Jul. 10, 2015.
Statement of Grounds and Particulars filed on Apr. 16, 2015, corresponding Australian Patent Application 2009252210.
Santen Oy Receives Marketing Authorization for TAFLOTAN®, a New Preservative-free Glaucoma Treatment in Denmark and Germany, Press Release Santen Oy (May 7, 2008).
Santen Oy Receives Marketing Authorization for its Glaucoma and Ocular Hypertension Treatment, TAFLOTANTM, in Denmark, News Release Santen Oy (May 7, 2008).
Decentralised Procedure Public Assessment Report: Taflotan 15 micrograms/ml eye drops, solution and solution, single dose container; Tafluprost; DE/H/0991/001-002/DC (Mar. 19, 2008).
Taflotan Summary of Product Characteristics—Denmark pp. 1-8 (Feb. 24, 2015).
Taflotan Summary of Product Characteristics—UK (Apr. 7, 2015) www.medicines.org.uk/emc/history/22237.
Taflotan Summary of Product Characteristics—UK with changes (Apr. 7, 2015).
Samalonis et al., Preservatives' Role in Topical Ocular Drugs, Review of Ophthalmology, pp. 1-4 (Sep. 14, 2006).
Baudouin et al., In Vitro Studies of Antiglaucomatous Prostaglandin Analouges: Travoprost with and without Benzalkonium Chloride and Preserved Latanoprost, 48(9) Invest Ophthalmol & Vis Sci, 4123-4128 (Sep. 2007).
Pisella et al., Prevalence of ocular symptoms and signs with preserved and preservative free glaucoma medication, 86 Br J Ophthalmol 418-423 (2002).
Furrer et al., Ocular tolerance of preservatives and alternatives, 53 European Journal of Pharmaceutics and Biopharmaceutics 263-280 (2002).
Ota et al., Prostaglandin Analogues and Mouse Intraocular Pressure: Effects of Tafluprost, Latanoprost, Travoprost and Unoprostone, Considering 24-Hour Variation, 46(6) Investigative Ophthalmology & Visual Science (Jun. 2005).
Traverso et al., A pilot phase II study on the extent, duration of action and stability of the IOP lowering effect of tafluprost 0.0015%, a novel prostaglandin analogue, as compared to latanoprost 0.005%, 143-03 Acta Ophthalmologica Scandina vica 36 (2006).
Epstein, Ocular Surface Disease and Antiglaucoma Pharmaceutics, Medscape Ophthalmology (May 27, 2008).
Hamacher et al., Efficacy and safety levels of preserved and preservative-free tafluprost are equivalent in patients with glaucoma or ocular hypertension: results from a pharmacodynamics analysis, 86 Acta Ophthalmologica 14-19 (2008).
Uusitalo et al., Pharmacokinetics, efficacy and safety profiles of preserved and preservative-free tafluprost in healthy volunteers, 86 Acta Ophthalmologica 7-13 (2008).
Baudouin, Detrimental effect of preservatives in eye drops: implications for the treatment of glaucoma, 86 Acta Ophthalmologica 716-726 (2008).
Rowe et al., Handbook of Pharmaceutical Excipients, 225-228 (2003).
Egorov et al., Adjunctive use of tafluprost with timolol provides additive effects for reduction in intraocular pressure in patients with glaucoma, 85(S240) Acta Ophthalmologica Scandinavica (Sep. 2007).
Egorov et al., Adjunctive use of tafluprost with timolol provides additive effects for reduction in intraocular pressure in patients with glaucoma, 19(2) Eur J Ophthalmol 214-22 (2009).
Notice of Filing Evidence in Support filed in the Australian Patent Office dated Jul. 16, 2015, for Australian Patent Application No. 2009252210.
Declaration of Clinical Associate Professor Ivan Goldberg dated Jul. 16, 2015.
Declaration of Ronald Harding dated Jul. 16, 2015.
Declaration of Helen Grimes dated Jul. 16, 2015.
Tosoh Research & Technology Review vol. 50, p. 49-53 (2006).
Brasnu et al., In Vitro Effects of Preservative-Free Tafluprost and Preserved Latanoprost, Travoprost, and Bimatoprost in a Conjunctival Epithelial Cell Line, 33 Current Eye Research 303-312 (2008).
DuoTrav, Drugs.com, https://www.drugs.com/uk/duotrav.html#print (Feb. 2, 2018).
Ganfort 0.3 mg/ml + 5mg/ml eye drops, solution, in single-dose container, Medicines.org, https://www.medicines.org.uk/emc/product/1239/smpc/print (Jan. 25, 2018).
Higginbotham et al., The Efficacy and Safety of Unfixed and Fixed Combinations of Latanoprost and Other Antiglaucoma Medications, 47(Supplement 1) Survey of Ophthalmology S133-S140 (Aug. 2002).
Opponent's Further Submissions in European Patent No. 1011728 B1, submitted on Feb. 22, 2007.
Kuppens et al., Effect of timolol with and without preservative on the basal tear turnover in glaucoma, 79 British Journal of Ophthalmology, 339-342 (1995).
Xalacom eye drops, solution, Medicines.org, https://www.medicines.org.uk/emc/medicine/7735/SPC/Xalacom+eye+drops,+solution/ (Feb. 2, 2018).
Schuman et al., Efficacy and Safety of a Fixed Combination of Travoprost 0.004%/Timolol 0.5% Ophthalmic Solution Once Daily

(56) References Cited

OTHER PUBLICATIONS of Open-Angle Glaucoma or Ocular Hypertension, 140(2) American Journal of Ophthalmology 242.e1-242.e11 (Aug. 2005).
Timoptic, Merck & Co., Inc., 1-7 (1986).
Datasheet for the Decision issued in EP Application No. 99931790.2 on May 19, 2011.
Communication of a notice of opposition issued in EP Patent Application No. 14001862.3-1114/2772249 dated Feb. 8, 2018.
Communication of notices of opposition issued in EP Patent Application No. 14001862.3-1114/2772249 dated Feb. 14, 2018.
Defendant's Brief (original in Korean—Hangul) with English Translation (May 12, 2016), in Korean Patent No. 854056.
Cover and Notification of Korea Pharmacopoeia, Text of Korea Pharmacopoeia, Seventh Edition, Ministry of Health and Welfare Notification No. 1997-92 [Exhibit B-1] with English Translation (Dec. 31, 1997), p. 16.
Intellectual Property Tribunal 7th Division Decision issued on Nov. 23, 2015 original in Korean (Hangul) in the case of Invalidation Trial of Korean Patent No. 854056 with English Translation.
"Manufacture of New Drugs" by Yeoung-Sun Gu, published in Mar. 15, 1983, p. 17, the last line to p. 18, line 5 original in Korean (Hangul), it was cited on p. 11, in the Intellectual Property Tribunal 7th Division Decision issued on Nov. 23, 2015 original in Korean (Hangul) in the case of Invalidation Trial of Korean Patent No. 854056 with English Translation.
International Search Report (PCT/ISA/210) dated Jul. 16, 2009, by Japanese Patent Office as the International Searching Authority for International Application No. PCT/JP2009/060211.
Written Opinion (PCT/ISA/237) dated Jul. 16, 2009, by Japanese Patent Office as the International Searching Authority for International Application No. PCT/JP2009/060211.
Administrative Answer issued in CN 1815617.7 on May 22, 2017 (No. 31135).
Administrative Judgment issued in CN 200980119724.5 on Jan. 26, 2018.
"Pharmaceutics" (For undergraduate majored in pharmacy),Editor-in-Chief: Bin Lu, China Medical Science and Technology Press, 1$^{st}$ Edition, Jan. 2003, cover page, copyright page, contents page, text pp. 334-342, issued in CN 200980119724.5 (original in Chinese and English Translation).
Examination Decision on Request for Invalidation (No. 31128) issued in CN 200980119724.5 on Jan. 22, 2017.
Yaoji et al., Ethylenediaminetetraacetic Acid Disodium Salt, The Extra Pharmaceutical Necessities (1993).
Bao, The First Ophthalmic Shares, www.cnpharm.com (Jul. 2005) (cited in CN 200980119724.5).
Adminstrative Reply issued in CN 200980119724.5 on May 22, 2017.
Notification of Acceptance of Request for Invalidation issued in CN 200980119724.5 on Jul. 1, 2016.
Pharmaceutical Science, 3-1 (pp. 174-179) and 3-2 (pp. 20-21) issued in KR 10-2003-7003605.
Reasons for Submission of Information submitted in KR 10-2003-7003605 on Sep. 22, 2016.
Reasons for Additional Submission of Information submitted in KR 10-2003-7003605 on Mar. 23, 2017.
Regulation of Pharmaceutical Approval, Notification and Review, Annex 13 (Ministry of Food and Drug Safety Notification) issued in KR 10-2003-7003605.
Reaulation on Stability Test of Pharmaceuticals, Article 3, issued in KR 10-2003-7003605 on Jun. 30, 2016.
Written Reply of Third Party (Statement of Opinion) issued in CN 200980119724.5 dated May 18, 2017.
Notification of Acceptance of Request for Invalidation issued in CN 01815617.7 dated Jul. 1, 2016.
Decision of Examination of the Request for Invalidation (No. 31135) issued in CN 01815617.7 on Jan. 22, 2017.
Statement of Opinion issued in CN 01815617.7(No. 31135) dated May 18, 2017.
Decision for Suite Against Appeal, Administrative Judgment, issued in CN 01815617.7 (No. 31135) dated Jan. 26, 2018.
The Theory and Practice of Industrial Pharmacy, Sterile Products 645 (1970), p. 644-645.
Philippine Office Action (Subsequent Substantive Examination Report dated Nov. 29, 2013, issue in corresponding Philippines Patent Application No. 1/2010/502677 (2 Pages).
Third Party Observations filed by Atlas Farmacéutica S.A. on Oct. 21, 2010 regarding Argentine Patent Application No. P090101912.
Urs Lichenstein, Blow-fill-Seal for Ophthalmic Packaging, Apr. 19, 2007, printed from www.iptonline.com/articles/public/page122noprint. pdf, Google date sheet, 3 Pages.
American Academy of Optometry (British Chapter), EDTA, May 11, 2004, printed from https://web.archive.org/web/20040511195127/http://www.academy.org.uk/pharmacy/edta/htm, 1 Page.
Zimmerman et al., *Timolol. A beta-adrenergic blocking agent from the treatment of glaucoma*, Arch Ophthalmol. 1977 95(4):601-4, printed from http://www.ncbi.nlm.nih.gov/pubmed/322648, 1 page, abstract only.
Rowe et al., Sodium Phosphate, Monobasic, 2006, Pharmaceutical Press, 5$^{th}$ Edition, 6 pages.
Pleadings of Administrative Proceeding submitted on Mar. 7, 2019 to Supreme People's court by Patent Reexamination Board of CNIPA in Retrial against Judgment No. JAF2194 regarding Chinese Invention Patent No. 01815617.7 with English Translation.
Statement of Opinion submitted on Mar. 14, 2019 to Supreme People's court by Jiangsu Hengrui Medicine Co., Ltd in Retrial against Judgment No. JAF2194 regarding Chinese Invention Patent No. 01815617.7 with English Translation.
*Pharmaceutics*, Lijia Zou, ed., China Medical Science and Technology Press, 1$^{st}$ edition, Dec. 1996, pp. 189-191.
*Practical Pharmaceutics*, Zuo Zhang, et al., ed., Heilongjiang Science and Technology Press, 1$^{st}$ edition, Nov. 1983, pp. 373-378.
*A Complete Collection of Pharmaceutical Excipients*, Mingsheng Luo, et al., ed., Sichuan Science and Technology Press, 1$^{st}$ edition in Chengdu, Jan. 1995, pp. 176-179.
Drug manufacture, Chapter 7. "Stabilization of drug preparation" (Mar. 20, 1995) Exhibit No. Eul 2 submitted to Patent Court by KIPO with respect to Korean Patent No. 10-0854056 with English translation.
Mullins, *Ophthalmic Preparations*, Chapter 87, Remington's Pharmaceutical Sciences, 17th edition 1553-1566 (1985).
Exhibit No. Eul-4, Detailed drug information of Taflotan eye drops (Tafluprost), submitted to Patent Court by KIPO with respect to Korean Patent No. 10-0854056 with English translations (Jun. 10, 2019).
Exhibit No. Eul 5-1, Detailed drug information of Rescular Eye Drops (Isopropyl Unoprostone) submitted to Patent Court by KIPO with respect to Korean Patent No. 10-0854056 with English translations (Jun. 10, 2019).
Exhibit No. Eul 5-2, Detailed drug information of Latano Eye Drops (Latanoprost) submitted to Patent Court by KIPO with respect to Korean Patent No. 10-0854056 with English translations (Jun. 10, 2019).
Exhibit No. Eul 5-3, Detailed drug information of Xalost-S Eye Drops (Latanoprost) submitted to Patent Court by KIPO with respect to Korean Patent No. 10-0854056 with English translations (Jun. 10, 2019).
Organic Chemistry, Chapter 11.5, "Characteristics of SN2 reaction" (Jan. 20, 1999) Exhibit No. Eul 6 submitted to Patent Court by KIPO with respect to Korean Patent No. 10-0854056 with English translations (Jun. 10, 2019).
The People's Republic of China Higher People's Court of Beijing Municipality Administrative Judgment issued on Jun. 6, 2018 involving CN 200980119724.5 (with English Translation).
Intellectual Property Tribunal and Appeal Board 7$_{th}$ Division Notice to File a Response for Correction with the English translation mailed on Sep. 12, 2018.
Intellectual Property Tribunal and Appeal Board 7$_{th}$ Division Trial Decision with the English translation dated Dec. 26, 2018.
Response Brief submitted to the Korean Patent Court on Jun. 10, 2019, with respect to Korean Patent No. 10-0854056 and an English translation of the Response Brief. (78 pages).

(56) References Cited

OTHER PUBLICATIONS

Patent Court Decision issued Jan. 9, 2020, by the Korean Patent Court with respect to Korean Patent No. 10-0854056 and an English translation of the Decision. (43 pages).
Further Submissions by Dr. Richard Cooke on Aug. 21, 2019, to the European Patent Office with respect to European Patent No. 2772249. (7 pages).
Decision revoking the European Patent (Art. 101(3)(b) EPC) and Provision of the minutes in accordance with Rule 124(4) EPC issued on Jan. 31, 2020, by the European Patent Office with respect to European Patent No. 2772249. (29 pages).
Response Brief submitted to the Korean Patent Court on Apr. 9, 2020, with respect to Korean Patent No. 10-0854056 and an English translation of the Response Brief. (15 pages).
Administrative Judgment by the Supreme People's Court of the People's Republic of China regarding Chinese Invention Patent No. 200980119724.5 and an English translation of the Judgment, May 27, 2020.
Administrative Judgment by the Supreme People's Court of the People's Republic of China regarding Chinese Invention Patent No. 01815617.7 and an English translation of the Judgment, Jun. 23, 2020.

\* cited by examiner

Tafluprost Absorption at 5 C

Tafluprost Absorption at 25 C

METHOD AND COMPOSITION FOR TREATING OCULAR HYPERTENSION AND GLAUCOMA

CROSS-REFERENCE TO RELATED APPLICATIONS

This application is a Divisional application of U.S. patent application Ser. No. 12/995,351, filed on Feb. 2, 2011, which is a U.S. National Stage Application pursuant to 35 U.S.C. § 371 of International Patent Application PCT/JP2009/060211, filed on May 28, 2009, and published as WO 2009/145356 on Dec. 3, 2009, which claims priority to EP Patent Application 08397513.6, filed on May 30, 2008, all of which are incorporated herein by reference in their entireties for all purposes.

TECHNICAL FIELD OF THE INVENTION

The present invention relates to a preservative-free ophthalmic aqueous composition containing prostaglandin (PG hereafter) F2α analogues for treating ocular hypertension and glaucoma, to a method for treating ocular hypertension and glaucoma by administering said composition to a subject in need of such treatment, and to a method for increasing aqueous solubility and improving stability of PGF2α analogues in an aqueous composition.

BACKGROUND OF THE INVENTION

PGF2α analogues have been widely used for the treatment of glaucoma and ocular hypertension because of their effectiveness in lowering intraocular pressure and their low systemic side effects. PGF2α analogues include all of the known PGF2α analogues for example tafluprost, latanoprost, isopropyl unoprostone, travoprost, bimatoprost and the analogues shown in U.S. Pat. Nos. 5,886,035, 5,807,892, 6,096,783.

Tafluprost is a new-generation, fluorinated PGF2α isopropyl ester analogue, which is a potent ocular hypotensive agent (EP 0 850 926).

A concentration of PGF2α analogues used for a treatment of glaucoma is very low. For example, the effective concentration of tafluprost from 0.0005 to 0.005 (w/v), preferably about 0.0015%, in an ophthalmic composition has been found to be sufficient for the treatment of ocular hypertension and glaucoma. However, as lipophilic substances PGF2α analogues such as tafluprost are liable to be absorbed to resinous (plastic) containers or bottles commonly used to store ophthalmic solutions, and thus the already low drug concentration in the ophthalmic solution may be further lowered.

Preservatives

Preservatives which exhibit sufficient antimicrobial effect on bacteria and fungi have traditionally been used in ophthalmic compositions. In addition to this, the preservatives are required to be stable and preferably to homogenize and stabilize the composition by interacting with the ingredients, for example by homogeneously dispersing or dissolving the ingredients into the vehicle or base (see EP 0 969 846, EP 1 916 002 and EP 1 547 599). Nowadays the most commonly used preservatives in commercially available ophthalmic solutions are benzalkonium chloride (BAK) and other quaternary ammonium salts. Other pharmaceutically acceptable preservatives for ophthalmic solutions are for example boric acid-polyol-zinc chloride (EP 1 115 406) or chlorine oxide compounds (EP 1 905 453), chlorhexidine gluconate, benzethonium chloride, sorbic acid, potassium sorbate, ethyl p-hydroxybenzoate and butyl p-hydroxybenzoate.

However, preservatives are also known as the major etiology of keratoconjunctive disorders, and for safety purpose, it is preferred that the concentration of a preservative such as benzalkonium chloride (BAK) is as low as possible. Preservative free ophthalmic solutions have also been developed.

On the other hand, BAK has contributed to the prevention of the degradation of prostaglandins and to the inhibition of absorption of prostaglandins to the resinous container walls. The absorption of tafluprost and other PGF2α analogues to the resinous container walls has been a problem especially with containers made of polyethylene. Due to its properties, such as sufficient flexibility, softness, good manufacturability and user-friendliness, polyethylene is the preferred material of choice for packaging of ophthalmic compositions, especially in unit dose form.

In addition, absorption of PGF2α analogues to the resinous container walls depends on surface area of the container walls. A unit dose preparation contains very small amount of ophthalmic compositions and the contact area of the preparation to the container is very large. Thus, absorption of PGF2α analogues to the container walls is a severe problem for unit dose preparations.

Therefore, before the present invention it has in practice been impossible to prepare stable, preservative-free ophthalmic solutions which contain PGF2α analogues and which can be packaged and stored in containers consisting essentially of polyethylene. According to EP 1011728, aqueous prostaglandin compositions packaged in polypropylene containers are more stable than those packaged in polyethylene containers. Based on the stability results of said publication, a skilled person is not encouraged to choose polyethylene but is likely to disallow it as container material, especially for all highly lipophilic compounds such as PGF2α analogues. Polypropylene-polyethylene copolymers comprising polyethylene as a minor component are also possible but not alluding to polyethylene as the sole material or as a major resin component (EP 1 829 545).

Furthermore, almost all of PGF2α analogues are practically insoluble in water. It is thus necessary to solve also the problem of solubility to water in order to formulate PGF2α analogues in ophthalmic solutions, especially for unit dose preparations. In EP 1 321 144 and US 2007/248697, a nonionic surfactant has been added to the ophthalmic solution to prevent a prostaglandin derivative from being adsorbed to a resinous container. Other attempts to compensate the difficulties in formulating highly lipophilic prostaglandin analogues in water have been described for example in EP 0 969 846, EP 1 666 043, EP 1 011 728 and WO 2007/042262 but they do not mention any preservative-free composition.

It is therefore an object of the present invention to provide an ophthalmic aqueous solution comprising PGF2α analogues and substantially no preservatives wherein the absorption of PGF2α analogues to the resinous containers consisting essentially of polyethylene is prevented and wherein said analogues remain soluble, stable and bioavailable in a preservative-free preparation. The aqueous ophthalmic solution according to the invention provides a significant clinical advantage as there is currently an unmet clinical need of preservative-free prostaglandin eye drops for glaucoma patients.

SUMMARY OF THE INVENTION

The present invention relates to an aqueous ophthalmic solution for treating ocular hypertension and glaucoma comprising PGF2α analogue as an active ingredient thereof which solution contains nonionic surfactant, stabilizing agent, and substantially no preservatives in a container consisting essentially of polyethylene.

The present invention also relates to a method for treating ocular hypertension and glaucoma, which method comprises administering an aqueous ophthalmic solution comprising PGF2α analogue as an active ingredient thereof to a subject in need of said treatment, wherein the ophthalmic solution contains nonionic surfactant, stabilizing agent, and substantially no preservatives.

Further, the present invention relates to the use of PGF2α analogue for manufacturing an ophthalmic aqueous solution for the treatment of ocular hypertension and glaucoma, wherein said solution contains nonionic surfactant, stabilizing agent, substantially no preservatives and is stored in a container consisting essentially of polyethylene.

Another object of the invention is a method for increasing aqueous solubility and improving stability of PGF2α analogues in an aqueous ophthalmic solution, comprising the steps of preparing an ophthalmic aqueous solution containing PGF2α analogue, nonionic surfactant, stabilizing agent and substantially no preservatives, and packaging the preservative-free ophthalmic solution in a container consisting essentially of polyethylene.

Within this description, "substantially no preservatives" or "preservative-free" means that the solution contains absolutely no preservatives, or the solution contains preservatives at a concentration that is undetectable or does not provide a preservative effect.

DETAILED DESCRIPTION OF THE INVENTION

Figure 1:
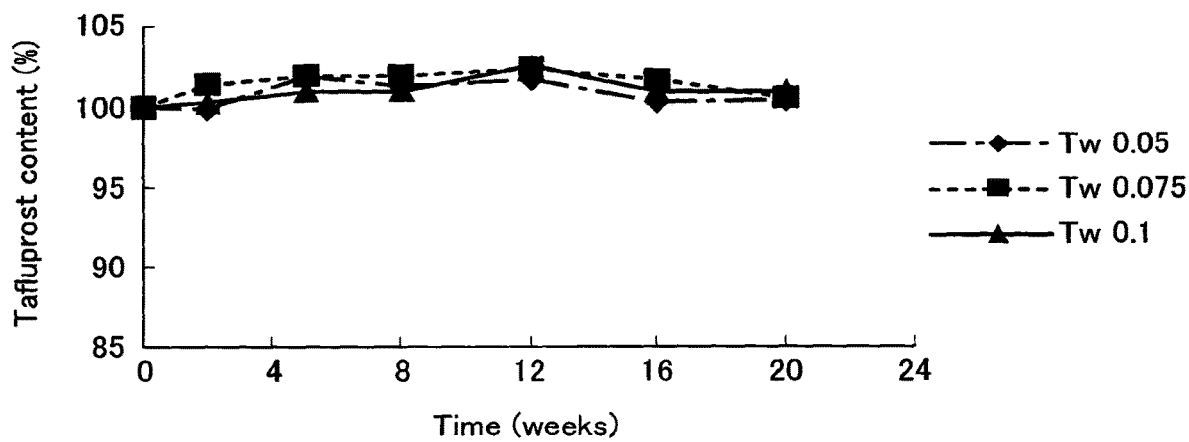
FIGS. 1-3 show the effect of polysorbate 80 (Tween 80; TW) on the absorption of preservative-free tafluprost to low-density polyethylene containers at three different concentrations of the polysorbate at 5° C., 25° C. and 40° C. respectively.

Nonionic surfactants are added to the ophthalmic solution according to the invention for their solubilizing effect and to prevent the absorption of PGF2α analogues to the resinous walls of the container. Examples of nonionic surfactants are polyoxyethylene fatty esters such as polysorbate 80 [poly (oxyethylene) sorbitan monooleate], polysorbate 60 [poly (oxyethylene)sorbitan monostearate], polysorbate 40 [poly (oxyethylene)sorbitan monopalmitate], poly(oxyethylene) sorbitan monolaurate, poly(oxyethylene)sorbitan trioleate and polysorbate 65 [poly(oxyethylene)sorbitan tristearate], polyoxyethylene hydrogenated castor oils such as polyoxyethylene hydrogenated castor oil 10, polyoxyethylene hydrogenated castor oil 40, polyoxyethylene hydrogenated castor oil 50 and polyoxyethylene hydrogenated castor oil 60, polyoxyethylene polyoxypropylene glycols such as polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Pluronic F127] and polyoxyethylene (20) polyoxypropylene (20) glycol [Pluronic L-44], polyoxyl 40 stearate and sucrose fatty esters. The nonionic surfactants can be used solely or in combination. A preferred example of the nonionic surfactants is polysorbate 80 [poly(oxyethylene)sorbitan monooleate]. Other preferred nonionic surfactants are polyoxyethylene hydrogenated castor oil 60 and polyoxyl 40 stearate.

The amount of nonionic surfactant(s) in the ophthalmic solution according to the invention can be chosen depending on the amount and type of prostaglandin analogue and the specific surfactant(s) and is within the skill of a person in the art. For polysorbate 80, the concentration is for example in the range of 0.05 to 0.5% (w/v), even more preferably 0.05 to 0.1%, and most preferably about 0.075%. It has also been found by the present inventors that a too high concentration of the nonionic surfactant has an irritative effect on the corneal epithelium layer and an adverse effect on the bioavailability of prostaglandin from the ophthalmic solution. For example in the case of tafluprost an upper limit of 0.5% of the nonionic surfactant polysorbate 80 is possible.

The ophthalmic solution according to the invention also contains stabilizing agents to inhibit decomposition of PGF2α analogues in the ophthalmic solution. Preferred examples of stabilizing agents are ethylenediaminetetraacetic acid and salts thereof, such as disodium edetate, and dibutylhydroxytoluenc. Also other stabilizing agents, such as sodium nitrite, ascorbic acid, L-ascorbic acid stearate, sodium hydrogensulfite, alphathioglycerin, erythorbic acid, cysteine hydrochloride, citric acid, tocopherol acetate, potassium dichloroisocyanurate, 2,6-di-t-butyl-4-methylphenol, soybean lecithin, sodium thioglycollate, sodium thiomalate, natural vitamin E, tocopherol, ascorbyl pasthyminate, sodium pyrosulfite, butylhydroxyanisole, 1,3-butylene glycol, pentaerythtyl tetrakis[3-(3,5-di-t-butyl-4-hydroxyphenyl)]propionate, propyl gallate, 2-mercaptobenzimidazole and oxyquinoline sulphate, may be used.

The amount of stabilizing agents in the ophthalmic solution according to the invention can be selected depending on the specific stabilizing agent and is within the skill of a person in the art. For example, when the stabilizing agent is disodium edetate, the concentration is usually 0.005 to 0.2% (w/v), preferably 0.01 to 0.1%, even more preferably about 0.05%.

A preferred PGF2α analogue for use in the ophthalmic aqueous solution according to the invention is tafluprost. However, all of the known PGF2α analogues, especially other omega chain phenyl ring-substituted PGF2α analogues such as latanoprost, travoprost and bimatoprost or a mixture of two or more prostaglandins may also be used. Alternative drugs for use in the ophthalmic aqueous solution according to the invention are other prostaglandins and their derivatives such as prostaglandin E and its analogues (see U.S. Pat. No. 6,344,477 and references therein). Combinations of prostaglandins or analogues and other eye drugs, for example β-blocking agents such as timolol, are also possible.

The amount of PGF2α analogues in the ophthalmic solution according to the invention can be selected depending on the specific prostaglandin in question, on the diseases to be treated and their symptoms. For tafluprost, an amount of for example 0.0001 to 0.01%, preferably about 0.0005 to 0.0025%, even more preferably 0.0010 to 0.0025% (w/v) is regarded to be sufficient. Preferable concentrations of other PGF2α analogues for treating glaucoma are 0.001 to 0.004% for travoprost, approximately 0.005% for latanoprost, about 0.03% for bimatoprost and about 0.15% for unoprostone.

The ophthalmic solution according to the invention may also comprise conventional excipients used in ophthalmic compositions, such as buffering agents, solvents, pH adjusters, tonicity agents and the like. Examples of suitable buffering agents include but are not limited to sodium dihydrogen phosphate dihydrate, boric acid, borax, citric acid, or ε-aminocaproic acid. Specific examples of tonicity agents include but are not limited to glycerol, sorbitol, mannitol and other sugar alcohols, propylene glycol, sodium chloride, potassium chloride and calcium chloride.

The pH of the ophthalmic aqueous solution according to the invention is preferably from 4 to 8, more preferably from 5 to 7. As pH adjusters, common pH adjusting agents such as sodium hydroxide and/or hydrochloric acid may be used.

The material of the resinous container consists essentially of polyethylene. The container material may contain minor amounts of other materials than polyethylene, for example polypropylene, polyethylene terephthalate, polyvinyl chloride, acrylic resins, polystyrene, polymethyl methacrylate and nylon 6. The amount of said materials is preferably no more than about 5 to 10% of the total container material. Polyethylene is classified to several types by the density thereof, namely low density polyethylene (LDPE), middle density polyethylene (MDPE), high density polyethylene (HDPE), etc and these polyethylenes are included in this invention. Preferable polyethylene is LDPE.

Containers for packaging and storing the aqueous ophthalmic solution according to the invention include all container forms suitable for user-friendly topical ophthalmic delivery. Consequently, the containers may be selected for example from the group consisting of bottles, tubes, ampoules, pipettes and fluid dispensers, in single unit dose form or in multidose form. According to a preferred embodiment of the invention, the aqueous ophthalmic solution is in a single dose or unit dose form.

The containers for the ophthalmic solution according to the invention are preferably manufactured by extrusion blow moulding method. Extrusion blow moulding gives smoother inner surface of the container compared to injection blow moulding, which is commonly used to manufacture for example polyethylene multidose bottles. The smoother inner surface gives better chemical stability of prostaglandins in the polyethylene container compared to polyethylene container manufactured by injection blow moulding. Furthermore, when single-dose containers are used, they are sterilized during the moulding process by heat and no additional sterilization of containers is needed, which also improves stability of prostaglandins in a single-dose container (see EP 1 825 855 and EP 1 349 580).

Generally, a unit dose ophthalmic container manufactured by blow moulding method has a volume of about 1 ml and about 0.2 to 0.5 ml of solution is filled. A large variety of shapes are known in such containers. Typical examples are seen in U.S. Pat. Nos. 5,409,125 and 6,241,124.

Although unit dose containers are preferred for the purposes of the invention, the aqueous ophthalmic solution according to the invention remains soluble, stable and bioavailable also in fluid dispensers for dispensing of minute amounts of germ-free fluid or in any other container-type wherein the aqueous ophthalmic solution is in contact with container material consisting essentially of polyethylene. Such fluid dispensers are disclosed for example in U.S. Pat. No. 5,614,172.

The preservative-free aqueous ophthalmic solution according to the invention can be stored at room temperature in the above mentioned suitable containers, including unit dose pipettes and dispensers. Stability studies have shown that a preservative-free aqueous ophthalmic tafluprost solution according to the invention is stable in a polyethylene container for a long time, at least for 12 months at 25° C. and at least for 30 months at 5° C.

A preferred embodiment according to the invention is an aqueous ophthalmic solution for treating ocular hypertension and glaucoma, which comprises
0.0001-0.01% w/v PGF2α analogues;
0.05-0.5% w/v non-ionic surfactant,
0.005-0.2% w/v stabilizing agent,
substantially no preservatives, and
optionally buffering agents, pH adjusters and tonicity agents conventionally used in ophthalmic solutions, in a container consisting essentially of polyethylene.

The following examples illustrate the invention without limiting the same any way.

Example 1

The effect of nonionic surfactant on the absorption of preservative-free tafluprost to low density polyethylene containers was studied for 20 weeks at 5° C., 25° C. and 40° C. Three different polysorbate 80 (Tween 80) concentrations, namely 0.05%, 0.075% and 0.1% were used. The composition of the preservative-free aqueous tafluprost formulation except polysorbate 80 was 0.0015% tafluprost, 2.25% glycerol, 0.2% sodium dihydrogen phosphate dihydrate, 0.05% disodium edetate and sodium hydroxide and/or hydrochloric acid to adjust the pH to 5.0-6.7.

0.3 ml of the composition prepared above was filled in the body part of the unit dose container (LDPE) and sealed by heating with the upper part of the container (LDPE). The inner volume of the unit dose container was ca. 1 ml. The container was packaged into paper coated aluminium-polyethylene foil and stored in refrigerator or incubator.

Figure 2:
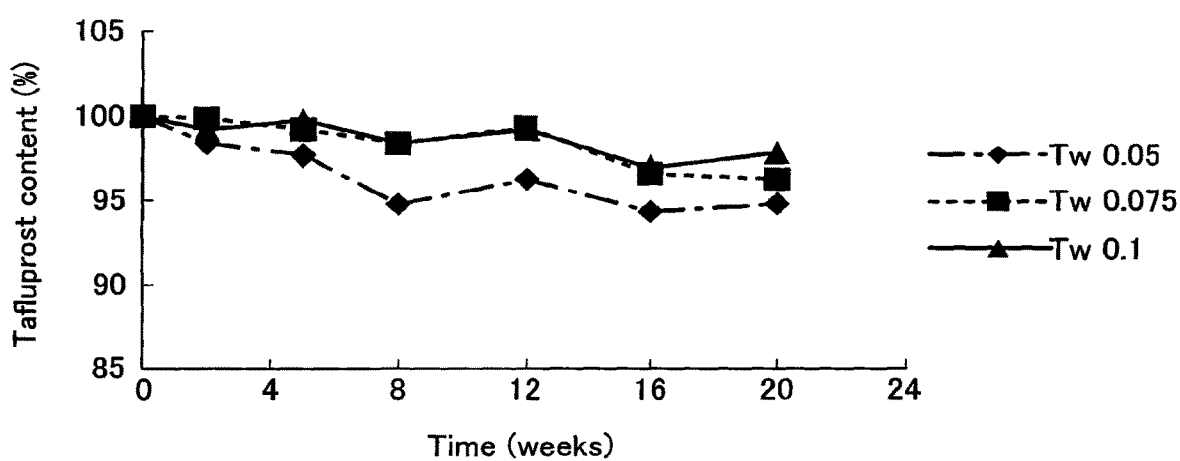
Figure 3:
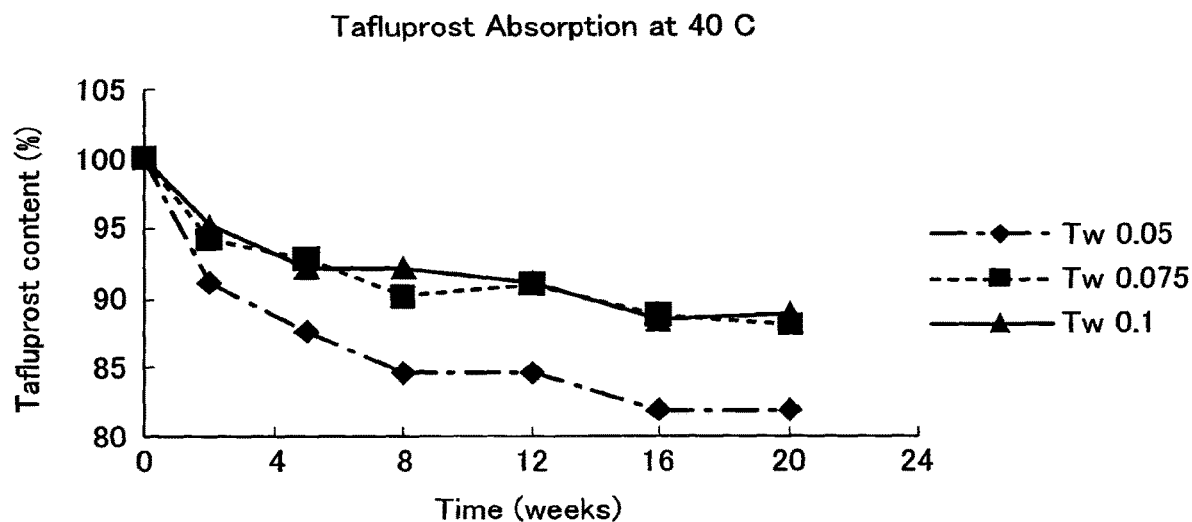

The remaining concentration of tafluprost was measured by HPLC. The results are shown in FIGS. 1-3. The results show that the concentration of polysorbate has an influence to the absorption of tafluprost to polyethylene. Polysorbate (0.05 to 0.1%) inhibits the absorption of tafluprost, especially even at an elevated temperature (40° C.). An amount of 0.075 to 0.1% of polysorbate shows good inhibition effect of absorption of tafluprost.

Example 2

The concentration of free acid of tafluprost in rabbit aqueous humor after a single instillation of
1) preserved 0.0015% tafluprost ophthalmic solution containing 0.01% BAK and 0.05% polysorbate 80, or
2) non-preserved 0.0015% tafluprost ophthalmic solution containing 0.20% polysorbate 80, or
3) non-preserved 0.0015% tafluprost ophthalmic solution containing 0.05% polysorbate 80
was studied.

The concentrations of ingredients except polysorbate 80 in non-preserved solutions were the following: 2.25% glycerol, 0.2% sodium dihydrogen phosphate dihydrate, 0.05% disodium edetate and sodium hydroxide and/or hydrochloric acid to adjust the pH to 5.0-6.7.

Rabbits received the ophthalmic solutions described above. The rabbits were sacrificed at each time point (4 animals per treatment per time point) and aqueous humor sample was taken. The concentration of tafluprost acid form was measured using the validated LC-MS/MS method.

Figure 4:
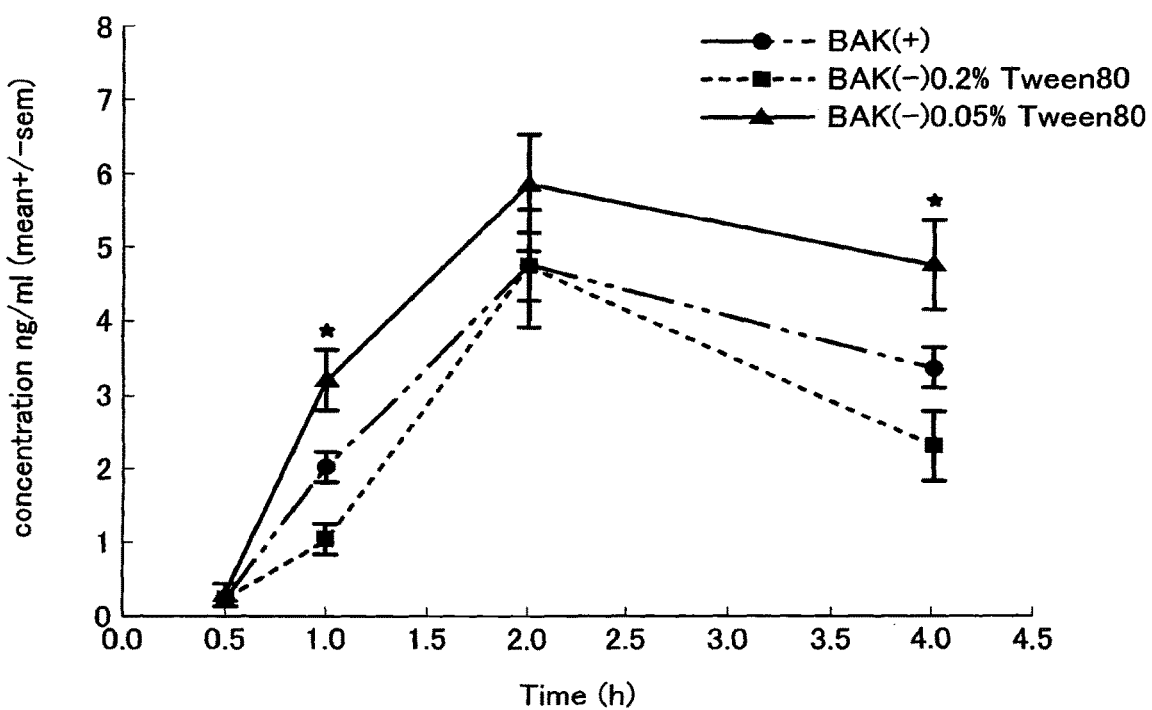
FIG. 4 shows concentration of acid form of tafluprost in rabbit aqueous humor after a single instillation of BAK-preserved 0.0015% tafluprost in ophthalmic solution [BAK (+)], non-preserved 0.0015% tafluprost ophthalmic solution containing 0.20% Tween 80 [BAK(−) 0.2% Tween 80], or non-preserved 0.0015% tafluprost ophthalmic solution containing 0.05% Tween 80 [BAK(−) 0.05% Tween 80]. Bars present standard error of the mean of tafluprost acid form concentration at each time point and asterisks represent statistically significant difference in tafluprost acid form concentrations between BAK(−) 0.2% Tween 80 and BAK (−) 0.05% Tween 80 solutions (p<0.05 with N=8).

The results (N=8 for each test solution per time point) are shown in FIG. 4. From the results it can be seen that the amount of nonionic surfactant has an effect on ocular bioavailability. When the amount of the nonionic surfactant exceeds a certain limit, penetration of the active agent to the aqueous humor starts to decrease. Thus the amount of the nonionic surfactant has to be balanced, on one hand to minimize the absorption of PGF2α analogue to the container walls and, on the other hand, to maximize ocular bioavailability.

The invention claimed is:

1. A method for treating ocular hypertension and glaucoma to a subject in need thereof, by administrating an ophthalmic aqueous solution consisting of 0.0015% w/v tafluprost as an active ingredient, 0.075% w/v polysorbate 80, 0.05% w/v disodium edetate, 2.25% w/v glycerol, 0.2% w/v sodium dihydrogen phosphate dihydrate, one or more pH adjusters, and water.

2. A method for treating ocular hypertension and glaucoma to a subject in need thereof according to claim 1, wherein the ophthalmic aqueous solution is packaged in a single dose or unit dose container.

3. A method for treating ocular hypertension and glaucoma to a subject in need thereof according to claim 1, wherein the ophthalmic aqueous solution is packaged in a container made of a low density polyethylene.

4. A method for treating ocular hypertension and glaucoma to a subject in need thereof according to claim 2, wherein the container is made of a low density polyethylene.

5. A method for treating ocular hypertension and glaucoma to a subject in need thereof according to claim 4, wherein the container contains no more than 10% of any material other than polyethylene.

* * * * *